(12) United States Patent
Phalke et al.

(10) Patent No.: US 8,090,189 B1
(45) Date of Patent: Jan. 3, 2012

(54) DETECTION OF THIN LINE FOR SELECTIVE SENSITIVITY DURING RETICLE INSPECTION

(75) Inventors: Vinayak Dattatreya Phalke, Portland, OR (US); Ge Cong, Pleasanton, CA (US); Lih-Huah Yiin, Mountain View, CA (US); Yalin Xiong, Union City, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 974 days.

(21) Appl. No.: 12/042,329

(22) Filed: Mar. 4, 2008

Related U.S. Application Data

(60) Provisional application No. 60/893,087, filed on Mar. 5, 2007.

(51) Int. Cl.
*G06K 9/00* (2006.01)

(52) U.S. Cl. .................................................. 382/144
(58) Field of Classification Search .................. 382/141, 382/144
See application file for complete search history.

(56) References Cited

U.S. PATENT DOCUMENTS

| 6,444,382 | B1 * | 9/2002 | Sarig et al. ............... 382/144 |
| 7,646,906 | B2 * | 1/2010 | Saidin et al. ............ 382/144 |

* cited by examiner

*Primary Examiner* — F. L. Evans
(74) *Attorney, Agent, or Firm* — Luedeka, Neely & Graham, P.C.

(57) ABSTRACT

Methods and apparatus relating to the inspection of photomasks are described. In an embodiment, detection of thin line or sub-resolution assist features may be used for selective sensitivity during photomask inspection. Other embodiments are also described.

18 Claims, 3 Drawing Sheets

DETECTION OF THIN LINE FOR SELECTIVE SENSITIVITY DURING RETICLE INSPECTION

RELATED APPLICATIONS

This application is related to and claims priority from the Provisional U.S. Patent Application Ser. No. 60/893,087, filed Mar. 5, 2007, entitled "Detection of Thin Line for Selective Sensitivity During Reticle Inspection," which is incorporated herein by reference for all purposes.

FIELD

The subject matter described herein generally relates to reticle inspection. In one embodiment, techniques described herein may detect thin line (e.g., sub-resolution assist features (SRAF)) for selectivity during reticle inspection.

BACKGROUND

When manufacturing integrated circuit devices, one or more photomasks or reticles may be used. Generally a photomask may be an opaque plate with transparencies that allow light to shine through a defined pattern. The patterns in the photomask may define the patterns found in an integrated circuit device. If there are defects in the pattern, the integrated circuit device may not function properly. In order to find defects in the pattern it is important that the inspection tool be able to distinguish between significant defects and insignificant defects.

BRIEF DESCRIPTION OF THE DRAWINGS

The accompanying drawings are included to provide further understanding of embodiments of the invention, illustrate various embodiments of the invention, and together with the description serve to explain the principles and operation of the invention. In the figures, the left-most digit(s) of a reference number identifies the figure in which the reference number first appears. The use of the same reference numbers in different figures indicates similar or identical items.

DETAILED DESCRIPTION

Figure 1:
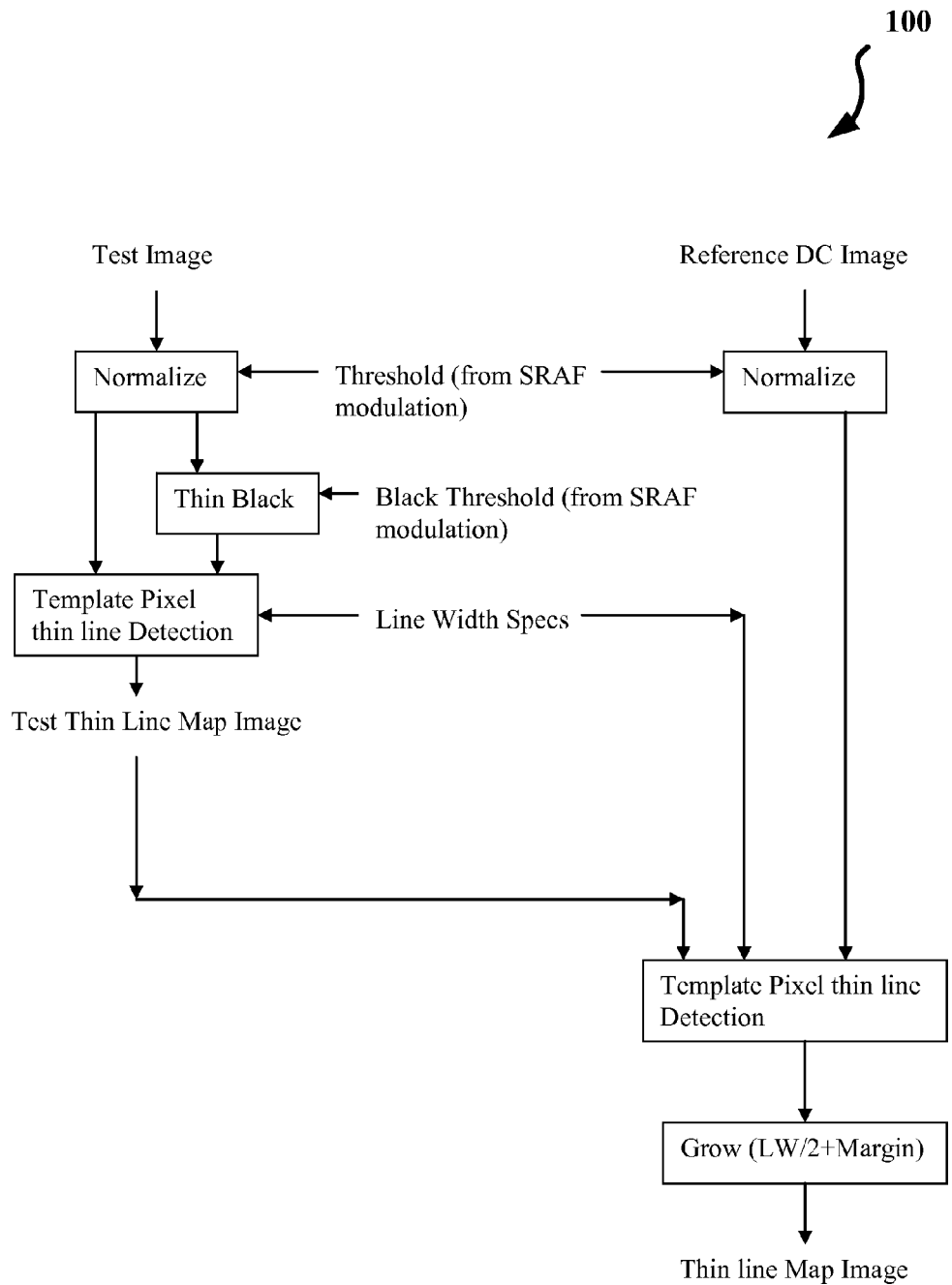
FIG. 1 illustrates a flow diagram of a method to detect thin lines, according to an embodiment.

In the following description, numerous specific details are set forth in order to provide a thorough understanding of embodiments of the invention. Embodiments of the invention may be practiced without some or all of these specific details. In other instances, well known process operations have not been described in detail in order not to unnecessarily obscure embodiments of the invention.

Also, reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Some embodiments discussed herein may provide a mechanism for the detection of sub-resolution assist features (SRAF) or thin lines on a photomask (which may be also referred to herein more generally as a "mask" or "reticle"). This detection then may allow for selective sensitivity selection such that defects on the reticles may be detected.

In one embodiment, an algorithm may use the rate of change of pixel intensity in the SRAF neighborhood to test for SRAF presence. For smaller line width (LW) SRAF, the pixel intensity may reach the nominal background faster (as a function of distance) than one which has larger LW. This profile of the pixel intensity may be pre-computed for a given LW limit for SRAF (the SRAF geometries will have LW smaller than a given LW) in an embodiment. As this involves pre-compute a template of fall off of pixel intensity, this detection may be referred to as "template pixel" approach. For example, if the edge profile is E(x) defined as function of x, the spatial distance from the center of edge, then the profile of the SRAF of line width LW, S(x), may be expressed as:

$$S(x)=E(x+LW/2)-E(x-LW/2)$$

One may also compute the inverse of this function, which defines the offset from edge for a given pixel intensity, Offset (I):

$$\text{Offset}(I)=\text{Inverse}(S(x))$$

This pre-computed SRAF profile and the offset function may then be used to test if a particular test pixel for SRAF is showing the same kind (or faster) of pixel intensity drop-off as the LW specification. In an embodiment, this may be done by checking the pixel intensity at two points in radially opposite direction with the same spatial offset. These pixel intensity may have offset smaller (or equal) than the spatial offset for the two locations.

Furthermore, an embodiment of the algorithm may include preprocessing and/or post-processing stages where depending on inspection mode (e.g., Die:Die, Die:Database or contamination), additional processing of input optical image will be done.

For example, for Die:Die and contamination inspection, the input for the SRAF detection may be an optical image from a relatively high resolution imaging system. These images may not have the same edge profile (e.g., the illumination spot function) due to focus variations and phase effects of the phase shift reticles. Thus, in such inspection modes, the input optical images may be preprocessed (e.g., normalized) to conform those images to have the same edge profile as the one used for the SRAF detection algorithm. The optimization for speed may be done by pre-computing potential target pixels for SRAF detection (e.g., rather than all pixels). In case of Die:Die inspections, the SRAF detection may also be cross checked between both test and reference die to suppress false detection. For the Die:Database inspections, the reference (from database) optical image may not require this normalization (as that image is already conforming to a given edge profile).

In embodiments where both transmitted and reflected optical images are available, one may choose the light mode optimal for the SRAF detection. The Opaque SRAF (MoSi or chrome features on quartz) may have better modulation in transmitted light and Clear SRAF (quartz features on MoSi or chrome), may have better modulation in reflected light. Thus, those light modes may be used for SRAF detection. The Die:Die (or contamination) SRAF detection algorithm may further implement this dual light mode detection.

FIG. 1 illustrates a flow diagram of a method 100 to detect thin lines, according to an embodiment. In one embodiment, the method 100 may be used to defect thin lines (such as sub-resolution assist features (SRAF)). Also, various operations discussed with reference to FIG. 1 may be performed by some of the components discussed herein, e.g., with reference to FIG. 2.

In some embodiments, the terms shown in FIG. 1 may be defined as follows:

(1) Normalization: Operation to change the edge speeds of the captured optical images to be same as that assumed in the Template Pixel SRAF detection algorithm.

(2) Thin Black: Operation to select potential test pixel locations for the Template Pixel SRAF detection algorithm to improve the algorithm throughput. Testing all pixels costs in terms of throughput and also this reduction/culling for the test pixel locations allows for avoiding the potential false positives of the Template Pixel SRAF detection algorithm Thin-Black operation involves detection of the skeleton of the thin line geometries as the test pixel using the contour level (pixel grayscale value) which defines the geometry edge for the line width (LW) definition.

(3) Template Pixel SRAF detection: The core SRAF (Thin Line) detection algorithm. This compares the rate of change of pixel intensity in the neighborhood of a test pixel (against the theoretical drop off for a SRAF of a given size, line width).

(4) Test and Reference Cross check for D:D: Due to presence of contamination or potential pattern defects which may mimic SRAF, if only one side of Die:Die (test or reference side) is used to find the SRAF pixel locations, one may have false positives for SRAF on such locations. This may be avoided by doing a cross checks between the two die (test and reference). By performing Template Pixel tests on test and/or reference sides, one may compute the SRAF map without such false hits. Note that the Die:Database inspection may not require this kind of cross-check because the database reference image will not have contamination or pattern defects.

(5) Enlarge ("Grow") SRAF Map: The SRAF or Thin Line Detection (TLD) may be done for the purpose of ability to separate out detected defects into those on main features (MF) and those on SRAF. This may be done because the SRAF may inherently have higher CD errors due to mask printing issues. Thus having the same CD error threshold for both MF and SRAF may lead to excessive defects on SRAF which may drown out defects which are important on MF (this is the reason for the differential sensitivity for defects on SRAF, as compared to the main features, for example). But the CD errors on SRAF may lead to situation which results in SRAF being of smaller size in test side as compared to reference (or vice versa) in Die:Die inspection, and thus detection SRAF map may require enlargement to grow the map to cover all potential SRAF pixels on both test and reference sides. The size of this SRAF map "growth" may be determined by the extent to which SRAF printing is not meeting requirements (and may be a user controlled parameter).

In some embodiments, a reticle inspection system may utilize embodiments discussed herein to provide the ability to distinguish detected defects between non-SRAF and SRAF defects and thus improve the overall defect disposition process for the die:die inspections. The same may be done for contamination and D:DB inspection modes.

In an embodiment, the following operations may provide a way to de-sense on small features while keeping high sensitivity on main features: (1) performing inspection in transmitted and reflected light modes (T and R) simultaneously; (2) a user may define a contour intensity grayscale value in transmitted images (where this value may be used to measure the dark feature line-width in transmitted images, thus de-sensing dark assist features); (3) a user may define a contour intensity grayscale value in reflected images (which may be used to measure the clear feature line-width in reflected images, thus de-sensing clear assist features); (4) allow assist features to be non-horizontal/vertical, and may be L-shaped or wavy (also, the ability to recognize the case where an assist feature has multiple line-width values may be provided, to enable de-sense performed on only a portion of a feature, whose line-width makes that portion a thin line, for example); (5) thin lines may be determined in both reference and test images (e.g., presence of a moderate-sized defect may not cause the thin line detector to label a main feature an assist); (6) differentiate thin line versus thin line-end; and/or (7) sensitivity sliders may be separate for T & R (e.g., if all sliders for T are zero, then no detection is done in T images, and vice versa, which may provide additional Die:Die transmitted light (ddT) and Die:Die reflected light (ddR) performance).

Figure 2:
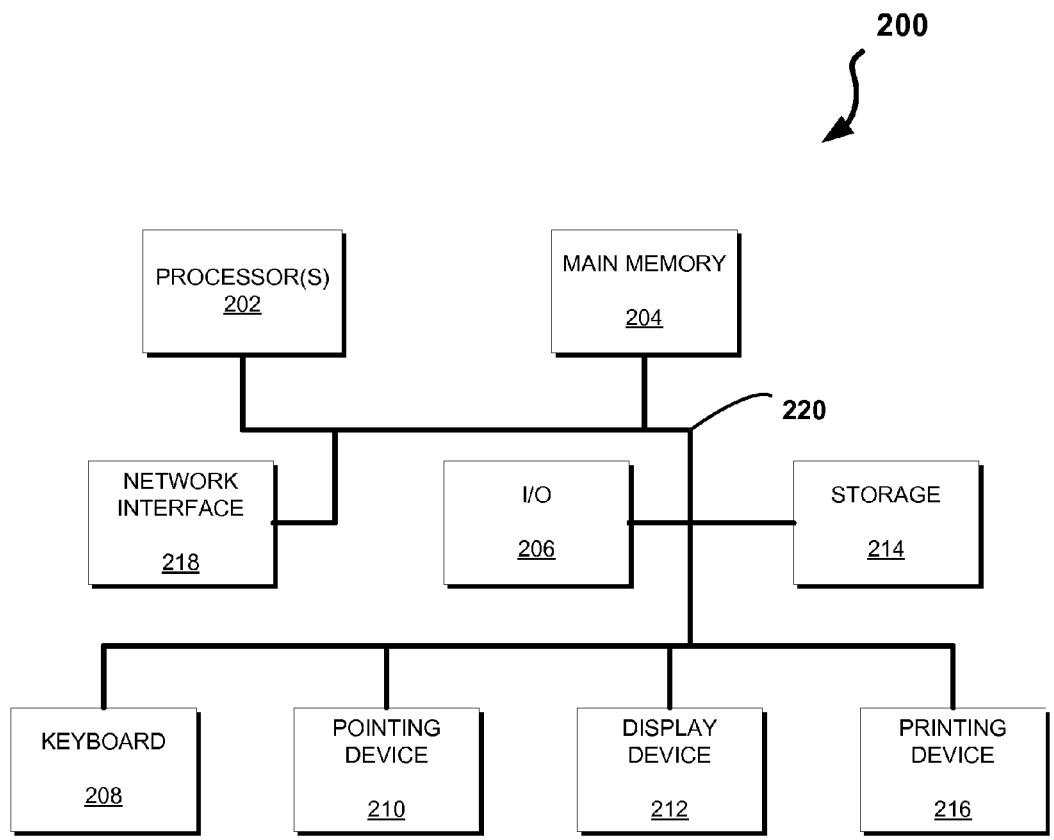
FIG. 2 illustrates a block diagram of computer system that may be utilized in various embodiments of the invention.

FIG. 2 illustrates a block diagram of computer system 200 that may be utilized in various embodiments of the invention. In an embodiment, the system 200 may be utilized to capture and/or manipulate one or more images discussed herein, for example. The system 200 may include one or more processors 202, a main memory 204, an input/output (I/O) controller 206, a keyboard 208, a pointing device 210 (e.g., mouse, track ball, pen device, or the like), a display device 212, a mass storage 214 (e.g., a nonvolatile storage such as a hard disk, an optical drive, or the like), and a network interface 218. Additional input/output devices, such as a printing device 216, may be included in the system 200 as desired. As illustrated in FIG. 2, the various components of the system 200 may communicate through a system bus 220 or similar architecture.

In accordance with an embodiment of the invention, the processor 202 may be a complex instruction set computer (CISC) microprocessor, a reduced instruction set computing (RISC) microprocessor, a very long instruction word (VLIW) microprocessor, or a processor implementing vector processing (or short vector processing), a processor implementing a combination of instruction sets, or the like.

Moreover, the network interface 218 may provide communication capability with other computer systems on a same local network, on a different network connected via modems or the like to the present network, or to other computers across the Internet. In various embodiments of the invention, the network interface 218 may be implemented by utilizing technologies including, but not limited to, Ethernet, Fast Ethernet, Gigabit Ethernet (such as that covered by the Institute of Electrical and Electronics Engineers (IEEE) 801.1 standard), wide-area network (WAN), leased line (such as T1, T3, optical carrier 2 (OC3), or the like), analog modem, digital subscriber line (DSL and its varieties such as high bit-rate DSL (HDSL), integrated services digital network DSL (IDSL), or the like), cellular, wireless networks (such as those implemented by utilizing the wireless application protocol (WAP)), time division multiplexing (TDM), universal serial bus (USB and its varieties such as USB II), asynchronous transfer mode (ATM), satellite, cable modem, and/or FireWire.

Moreover, the computer system 200 may utilize operating systems such as Solaris, Windows (and its varieties such as CE, NT, 2000, XP, ME, Vista, or the like), HP-UX, IBM-AIX, PALM, UNIX, Berkeley software distribution (BSD) UNIX, Linux, Apple UNIX (AUX), Macintosh operating system (Mac OS) (including Mac OS X), a variant of embedded operating systems, or the like. Also, in certain embodiments of the invention, the computer system 200 may be a general purpose computer capable of running any number of applications.

Figure 3:
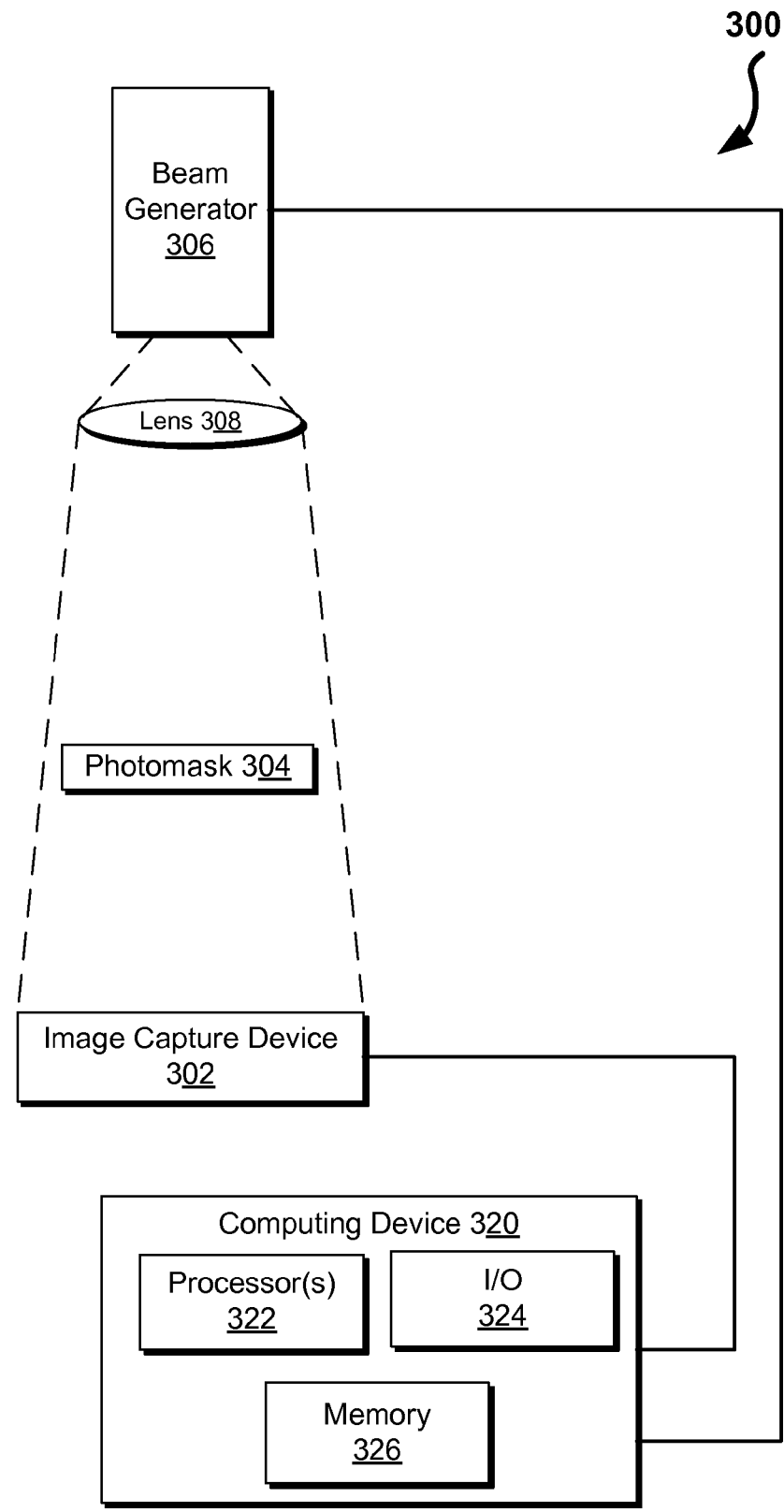
FIG. 3 illustrates a block diagram of an inspection system that may be utilized in various embodiments of the invention.

FIG. 3 illustrates a block diagram of an inspection system 300 in accordance with an embodiment of the invention. In various embodiments, the system 300 may be used to detect photomask (which may be also referred to herein more generally as a "mask" or "reticle") defects, such as discussed further herein with reference to FIG. 1, for example.

As shown in FIG. 3, the system 300 may include an image capture device 302 to capture an image of a photomask 304. The photomask 304 may be patterned by a pattern generating tool (not shown). The device 302 may capture an image of the photomask 304 using a beam generator 306 which may be any type of a beam generator such as an optical beam generator or an electron beam generator. In an embodiment, the system 300 may optionally include a lens 308 to focus the beam generated by the beam generator 306. Also, the lens 308 may include more than a single lens in some embodiments. Furthermore, the lens 308 may be provided at various locations. For example, the lens 308 may be provided between the beam generator 306 and the photomask 304 (as shown in FIG. 1). Alternatively, the lens 308 may be provided between the photomask 304 and the image capture device 302. Also, in multiple lens systems, one or more of the lenses may be provided between the generator 306 and the photomask 304, between the photomask 304 and the device 302, or any combinations thereof.

The system 300 may additionally include a computing device 320 to control some or all of the operations of the system 300, as will be further discussed herein, for example, with reference to FIG. 1. Alternatively, a standalone computing device (such as that discussed with reference to FIG. 2) may be used to perform reticle analysis offline from reticle inspection system. The computing device 320 may include one or more processors 322, an input/output (I/O) module 324, and/or a memory 326 (which may be a volatile and/or nonvolatile memory). For example, the I/O module 324 may communicate with various components of the system 300, while the processors 322 may process the communicated data and the memory 326 may store the communicated data, as will be further discussed herein, e.g., with reference to FIG. 1. As shown in FIG. 3, the computing device 320 may control and/or communicate with the beam generator 306 and/or the image capture device 302. For example, the computing device 320 may cause the beam generator 306 to generate a beam at a desired wavelength and/or for a certain time period. Moreover, the computing device 320 may cause the image capture device 302 to capture an image of the photomask 304 for further processing, such as discussed with reference to FIG. 1.

In various embodiments of the invention, the operations discussed herein, e.g., with reference to FIGS. 1-3, may be implemented as hardware (e.g., logic circuitry), software, firmware, or combinations thereof, which may be provided as a computer program product, e.g., including a machine-readable or computer-readable medium having stored thereon instructions (or software procedures) used to program a computer to perform a process discussed herein. The machine-readable medium may include any suitable storage device such as those discussed with respect to FIGS. 2 and 3.

Additionally, such computer-readable media may be downloaded as a computer program product, wherein the program may be transferred from a remote computer (e.g., a server) to a requesting computer (e.g., a client) by way of data signals embodied in a carrier wave or other propagation medium via a communication link (e.g., a modem or network connection).

In the description and claims, the terms "coupled" and "connected," along with their derivatives, may be used. In some embodiments of the invention, "connected" may be used to indicate that two or more elements are in direct physical contact with each other. "Coupled" may mean that two or more elements are in direct physical contact. However, "coupled" may also mean that two or more elements may not be in direct contact with each other, but may still cooperate or interact with each other.

Although embodiments have been described in language specific to structural features and/or methodological acts, it is to be understood that claimed subject matter may not be limited to the specific features or acts described. Rather, the specific features and acts are disclosed as sample forms of implementing various embodiments. While the invention has been described above in conjunction with one or more specific embodiments, it should be understood that the invention is not intended to be limited to one embodiment. The invention is intended to cover alternatives, modifications, and equivalents as may be included within the spirit and scope of the invention, such as those defined by the appended claims.

The invention claimed is:

1. An apparatus comprising:
    an image capture device to capture an image of a photomask; and
    logic to;
        detect a thin line based on the captured image, wherein the thin line corresponds to at least one sub-resolution assist feature (SRAF), and
        select a sensitivity of an inspection of the photomask based on the SRAF.

2. The apparatus of claim 1, wherein the logic is to compare a rate of change of a pixel intensity in an area of a test pixel of the captured image against a theoretical drop off for the SRAF, wherein the theoretical drop off is pre-computed based on a given line width limit for the SRAF.

3. The apparatus of claim 1, wherein the logic is to normalize the captured image by changing zero or more edge speeds of the captured image to be the same as that of a select value.

4. The apparatus of claim 1, wherein the logic is to select one or more potential test pixel locations to improve throughput.

5. The apparatus of claim 1, wherein the logic is to cross-check a pixel location of the SRAF between a test die and a reference die to reduce false positives for the SRAF.

6. The apparatus of claim 1, wherein the logic is to enlarge a detection SRAF map to cover potential pixels of the SRAF on both a test die and a reference die.

7. The apparatus of claim 1, wherein the captured image is a transmitted light image, a reflected light image, or combinations thereof.

8. The apparatus of claim 1, wherein the logic comprises at least one processor.

9. A method comprising:
    detecting a thin line based on a captured image of a photomask, wherein the thin line corresponds to one or more sub-resolution assist features (SRAF); and
    selecting a sensitivity of an inspection of the photomask, based on the thin line.

10. The method of claim 9, wherein detecting the thin line comprises:
    comparing a rate of change of a pixel intensity in an area of a test pixel of the captured image against a theoretical drop off for the SRAF, wherein the theoretical drop off is pre-computed based on a given line width limit for the SRAF.

11. The method of claim 9, further comprising normalizing the captured image by changing zero or more edge speeds of the captured image to be the same as that of a selected value.

12. The method of claim 9, further comprising selecting one or more potential test pixel locations to improve throughput during reticle inspection.

13. The method of claim 9, further comprising cross-checking a pixel location of the SRAF between a test die and a reference die to reduce false positives for the SRAF.

14. The method of claim 9, further comprising enlarging a detection SRAF map to cover potential pixels of the SRAF on both a test die and a reference die.

15. The method of claim 10, wherein the comparison is performed based on a transmitted light image when analyzing the SRAF when it is opaque.

16. The method of claim 10, wherein the comparison is performed based on a reflected light image when analyzing the SRAF when it is clear.

17. A tangible computer-readable medium comprising one or more instructions that when executed on a processor configure the processor to perform one or more operations to:

detect a thin line based on a captured image of a photomask, wherein the thin line corresponds to one or more sub-resolution assist features (SRAF); and select a sensitivity of an inspection of the photomask based on the thin line.

18. The tangible computer-readable medium of claim 17, wherein the one or more instructions configure the processor to compare a rate of change of a pixel intensity in an area of a test pixel of the captured image against a theoretical drop off for the SRAF, wherein the theoretical drop off is pre-computed based on a given line width limit for the SRAF.

* * * * *